(12) United States Patent
Fairneny et al.

(10) Patent No.: US 9,283,063 B2
(45) Date of Patent: Mar. 15, 2016

(54) MEDICAL DEVICE AND METHODS OF DELIVERING THE MEDICAL DEVICE

(75) Inventors: Ty Fairneny, Hopkinton, MA (US); Dennis Miller, Whitefish Bay, WI (US); Michael F. Weiser, Groton, MA (US)

(73) Assignee: Boston Scientifique Scimed, Inc., Maple Grove, MN (US)

( * ) Notice: Subject to any disclaimer, the term of this patent is extended or adjusted under 35 U.S.C. 154(b) by 227 days.

(21) Appl. No.: 13/608,919

(22) Filed: Sep. 10, 2012

(65) Prior Publication Data

US 2013/0061855 A1    Mar. 14, 2013

Related U.S. Application Data

(60) Provisional application No. 61/533,586, filed on Sep. 12, 2011.

(51) Int. Cl.
*A61F 6/08*    (2006.01)
*A61F 2/00*    (2006.01)

(52) U.S. Cl.
CPC ............ *A61F 2/0045* (2013.01); *A61F 2/0063* (2013.01); *A61F 2250/006* (2013.01); *A61F 2250/0097* (2013.01)

(58) Field of Classification Search
USPC .......... 128/830–834, 838, 897–898, DIG. 25; 606/99, 151; 623/23.72; 600/29–31, 37
See application file for complete search history.

(56) References Cited

U.S. PATENT DOCUMENTS

| | | | |
|---|---|---|---|
| 6,575,897 B1 * | 6/2003 | Ory et al. | 600/30 |
| 8,057,382 B2 * | 11/2011 | Thierfelder et al. | 600/30 |
| 8,109,866 B2 * | 2/2012 | Bouchier et al. | 600/30 |
| 2008/0021265 A1 | 1/2008 | Garbin et al. | |
| 2009/0171142 A1 * | 7/2009 | Chu | 600/37 |
| 2009/0318752 A1 * | 12/2009 | Evans et al. | 600/37 |
| 2010/0081865 A1 | 4/2010 | Hamati | |
| 2010/0191038 A1 * | 7/2010 | Kubalak et al. | 600/30 |
| 2010/0305394 A1 | 12/2010 | Rosenblatt | |

(Continued)

FOREIGN PATENT DOCUMENTS

| | | |
|---|---|---|
| EP | 2340784 A1 | 7/2011 |
| WO | 2009018372 A2 | 2/2009 |
| WO | 2010087923 A1 | 8/2010 |

(Continued)

OTHER PUBLICATIONS

Search Report and Written Opinion for International Application No. PCT/US2012/054642, mailed Sep. 17, 2013, 16 pages.

(Continued)

*Primary Examiner* — Ophelia A Hawthorne
(74) *Attorney, Agent, or Firm* — Brake Hughes Bellermann LLP

(57) ABSTRACT

A medical device and methods of delivery of the medical device within a patient's body are disclosed by the present invention. The medical device includes a first elongate member, a second elongate member and a coupling member. The coupling member is configured to be coupled to and extend between the first elongate member and the second elongate member to couple the first elongate member to the second elongate member when the medical device is in a first configuration. The coupling member is configured to be decoupled from at least one of the first elongate member and the second elongate member when the medical device is in a second configuration.

19 Claims, 13 Drawing Sheets

(56) References Cited

U.S. PATENT DOCUMENTS

2011/0105836 A1  5/2011  Miller
2012/0151516 A1  6/2012  Yanko

FOREIGN PATENT DOCUMENTS

| WO | 2010138894 A2 | 12/2010 |
| WO | 2013039899 A2 | 3/2013 |
| WO | 2013039899 A3 | 11/2013 |

OTHER PUBLICATIONS

"Laparoscopic and Abdominal Sacrocolpopexy", Birmingham Women's Health Care, 4 pages.

"Surgical Repair of Vaginal Wall Prolapse Using Mesh", National Institute for Health and Clinical Excellence, Jun. 2008, 6 pages.

Carey, et al, "Vaginal Surgery for Pelvic Organ Prolapse Using Mesh and a Vaginal Support Device", Genitourinary Medicine, Oct. 23, 2007, 7 pages.

Elghazawy, "Abdominal (Mesh) Sacrocolpopexy", Trafford Healthcare, Patient Information Leaflet, Jan. 2, 2007, 2 pages.

Hextall, "SACROCOLPOPEXY", Information for Patients, Jul. 2008, 4 pages.

Xiromeritis, et al, "Outcome of laparoscopic sacrocolpopexy with anterior and posterior mesh". Hippokratia 2009, pp. 101-105.

International Preliminary Report on Patentability for International Application No. PCT/US2012/054642, mailed Mar. 20, 2014, 10 pages.

\* cited by examiner

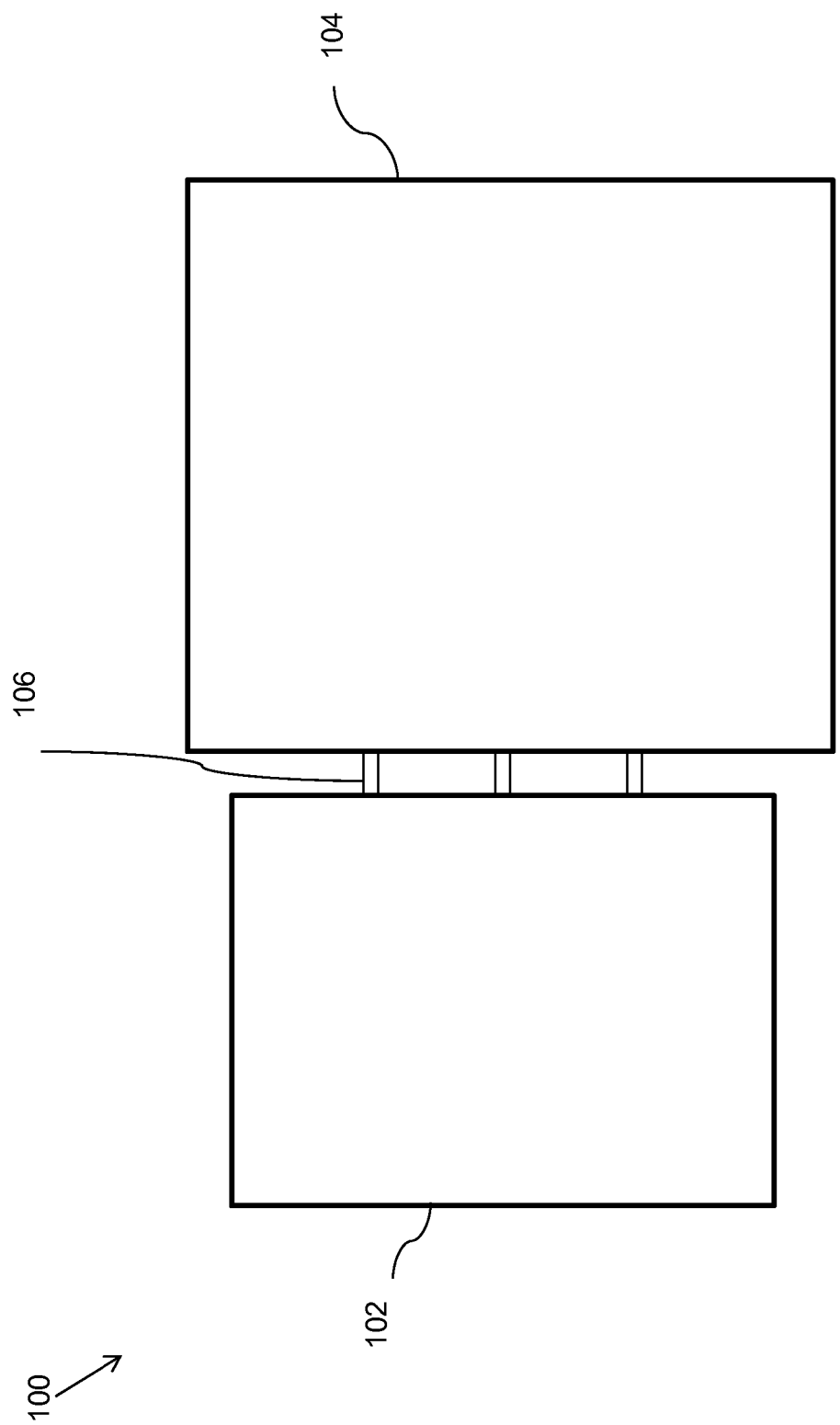

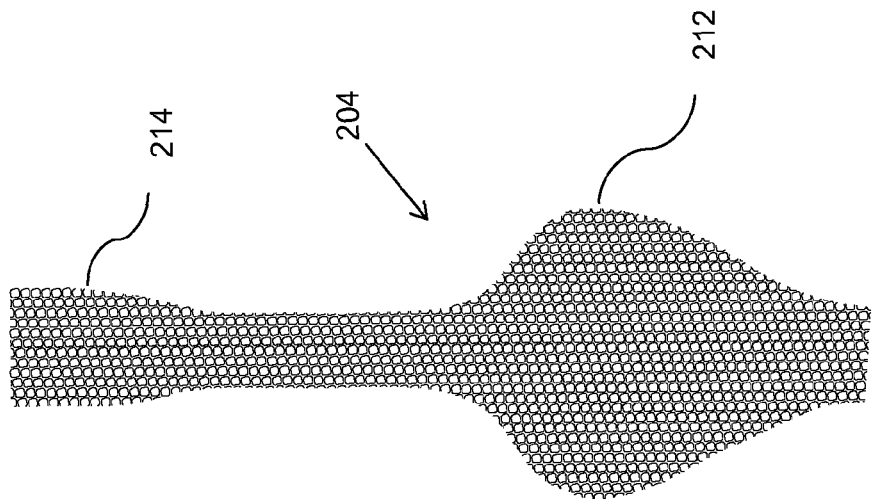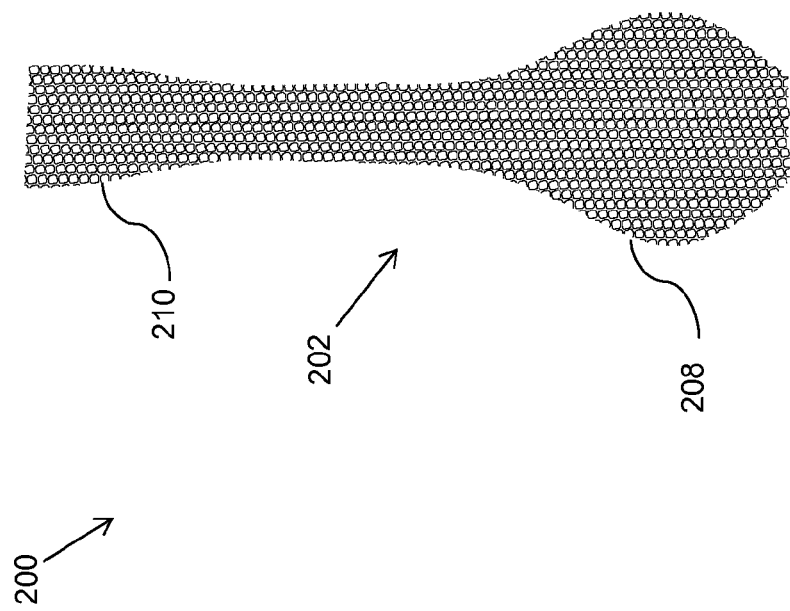
Fig. 2B

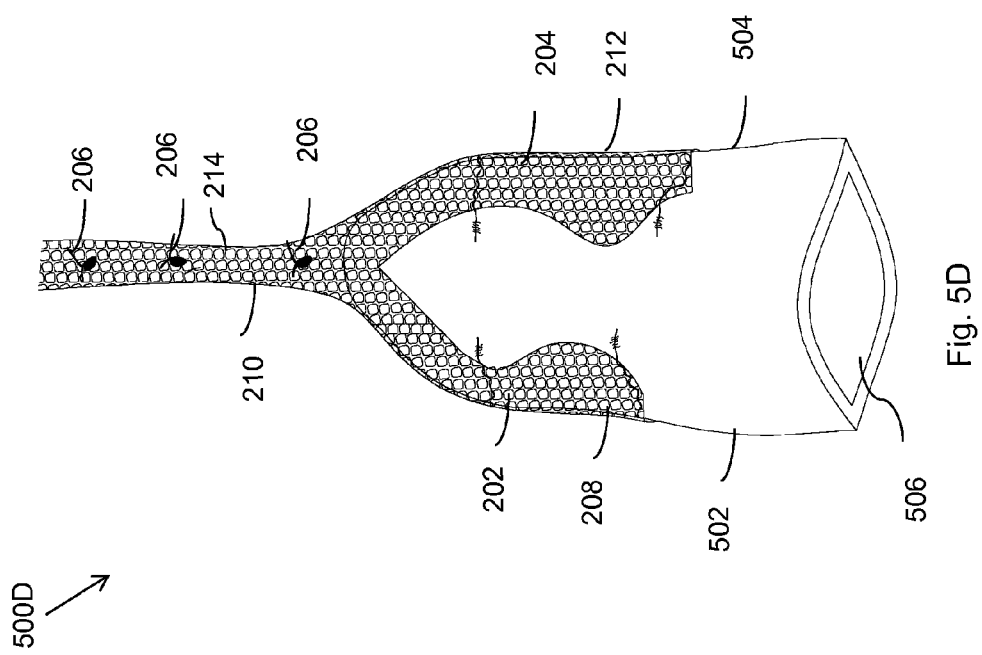

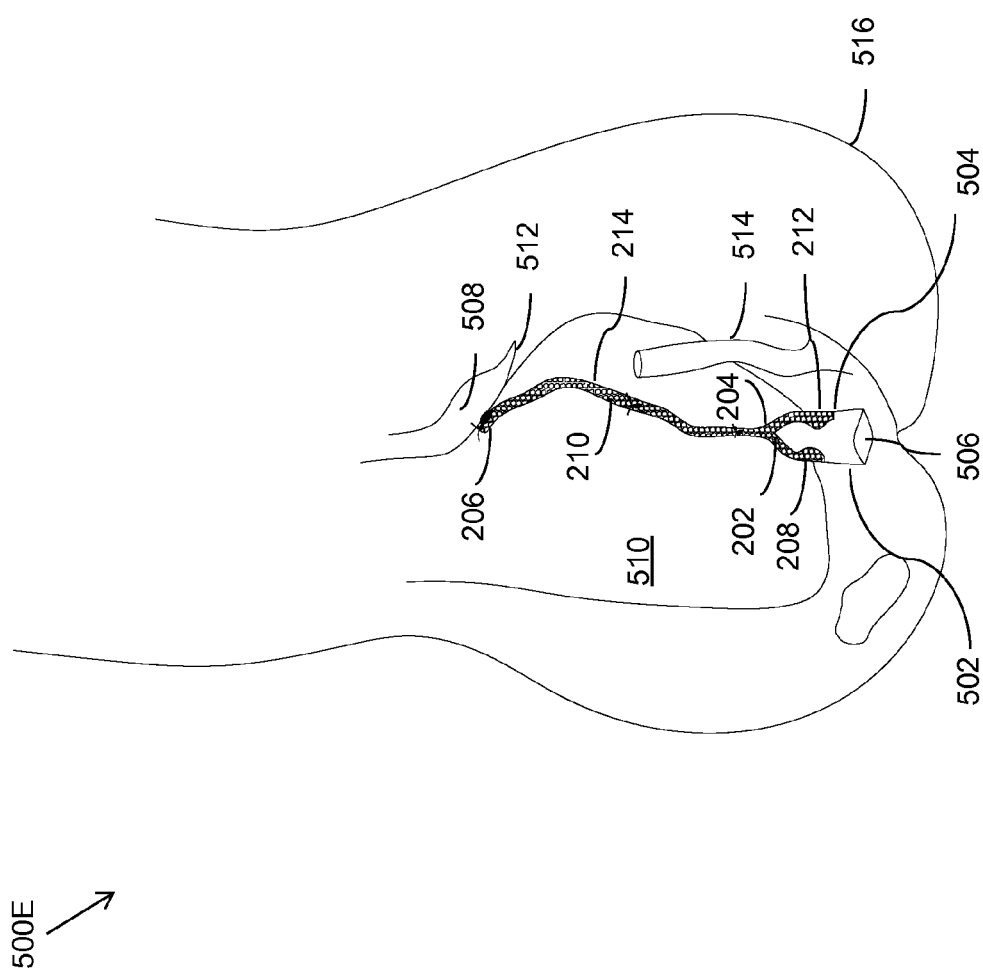

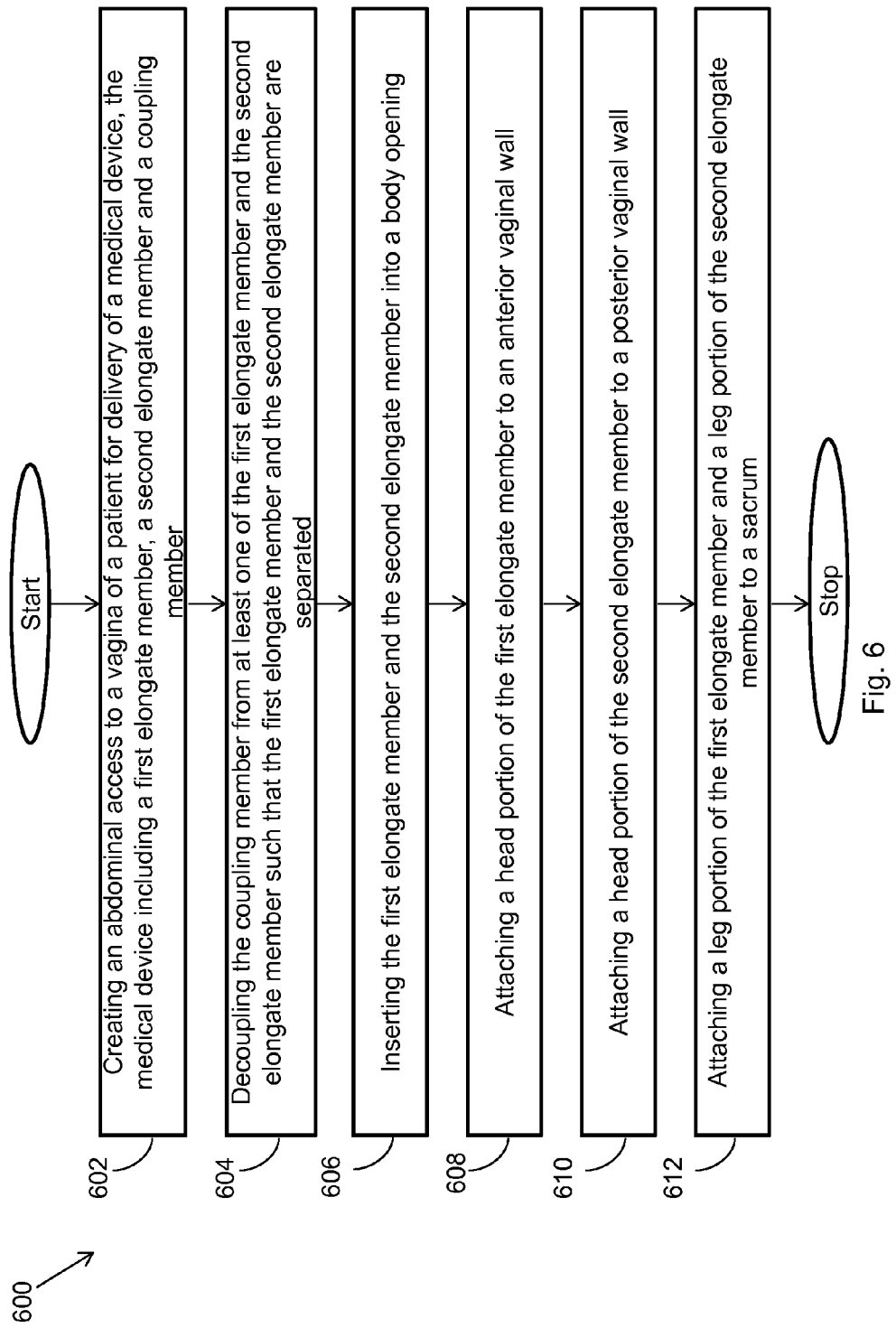

MEDICAL DEVICE AND METHODS OF DELIVERING THE MEDICAL DEVICE

CROSS-REFERENCE TO RELATED APPLICATION

This application is a Nonprovisional of, and claims priority to, U.S. Patent Application No. 61/533,586, filed Sep. 12, 2011, entitled "A MEDICAL DEVICE AND METHODS OF DELIVERING THE MEDICAL DEVICE", which is incorporated by reference herein in its entirety.

BACKGROUND

1. Field

The present invention generally relates to medical devices and procedures, particularly devices and methods for delivery and placement of the medical devices into a patient's body for the treatment of pelvic organ prolapse.

2. Description of the Related Art

Genital prolapse or pelvic organ prolapse is a common health issue that affects the quality of life of an individual. The repair of these pelvic organ defects is challenging and requires preoperative evaluation, knowledge of anatomy and surgical techniques. Some cases of pelvic organ prolapse may be a result of damages to the vaginal and pelvic support tissues due to childbirth or chronically elevated intra-abdominal pressure. Patients may notice a mass or protrusion from the vagina followed by pelvic pressure and backache. Some patients may also have one or more symptoms of urinary incontinence, urinary retention, sexual dysfunction, and difficulty with bowel movements.

Treatment of different types of pelvic organ prolapse may require surgery in order to provide support to the prolapsed organ via slings, mesh-based devices, and other kinds of implants. With advancements in medical technology, a variety of such devices are being considered for implantation into the patient's body for surgery. Also, various techniques of and procedures for delivering and placing these implants into the patient's body have evolved in the last few decades to treat pelvic organ prolapse.

Various shapes of the implants are available to meet the requirements of surgery as decided/preferred by a doctor/operator. Some implants used to treat prolapse and other pelvic organ disorders have a Y-shaped configuration. Such implants may include two arms that are placed from the anterior and posterior sides of the vagina to one of the bones at the back of the pelvis such as the sacrum.

The existing Y-shaped implants can be used to support the anterior and posterior vaginal walls with a uniform tension upon placement within the bodily tissues. In such implants, the tension in one arm is dependent on the other arm; therefore, providing specific tensions to the two arms separately is difficult. However, as per the surgical requirements, various doctors/operators may prefer a particular approach to repair the pelvic damage. Some would opt to secure the implant with different and specific tensions at posterior and anterior walls, whereas others would prefer to secure the implant with uniform tension at the anterior and posterior walls. These implants, however, are not capable of being converted or customized for both types of surgical requirements decided by the doctor or the operator.

Thus, there is a need for a single medical device or an implant that may be customized as per the surgical requirements.

SUMMARY

A medical device and methods of delivery of the medical device within a patient's body are disclosed by the present invention. The medical device includes a first elongate member, a second elongate member and a coupling member. The first elongate member further includes a leg portion and a head portion. The head portion is configured to be attached to a first bodily portion and the leg portion is configured to be attached to second bodily portion. The second elongate member includes a leg portion and a head portion. The head portion of the second elongate member is configured to be attached to a third bodily portion and the leg portion of the second elongate member is configured to be attached to a fourth bodily portion. The coupling member is configured to be coupled to and extend between the first elongate member and the second elongate member to couple the first elongate member to the second elongate member when the medical device is in a first configuration. The coupling member is configured to be decoupled from at least one of the first elongate member and the second elongate member when the medical device is in a second configuration.

BRIEF DESCRIPTION OF THE FIGURES

The invention and the following detailed description of certain embodiments thereof may be understood with reference to the following figures:

FIG. 1 is a schematic diagram of a medical device configured to be implanted within a patient's body, in accordance with an embodiment of the present invention.

FIG. 2B is a top view a medical device in a decoupled configuration, in accordance with an embodiment of the present invention.

FIGS. 5D-5F illustrate schematic views of placement of a medical device in the first configuration (coupled configuration), in accordance with an embodiment of the present invention.

FIG. 6 is a flowchart illustrating a method of placement of a medical device, in accordance with an embodiment of the present invention.

DETAILED DESCRIPTION

Figure 2A:
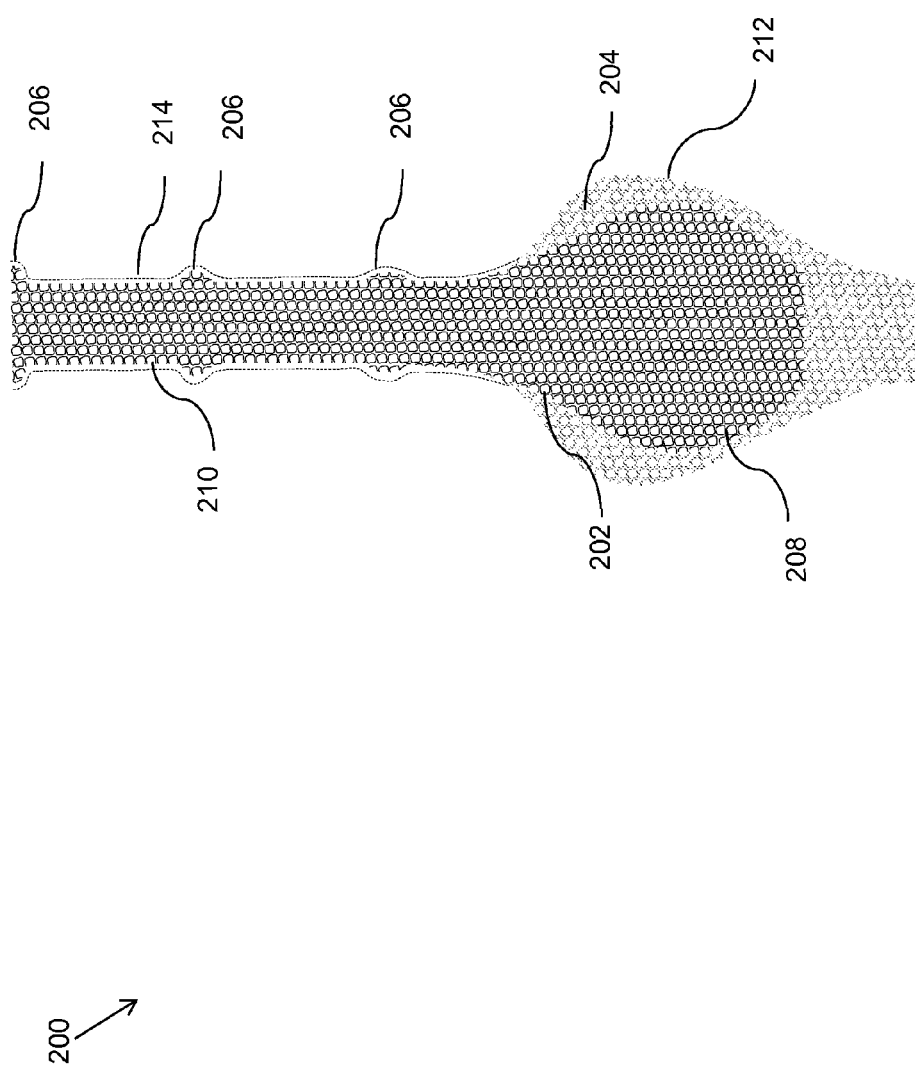
FIG. 2A is a top view of a medical device in a coupled configuration, in accordance with an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating vaginal prolapse. However, the invention may be equally employed for other treatment purposes such as pelvic organ prolapse. As described below in various illustrative embodiments, the invention provides systems, methods, and devices employing an improved medical device configured to be implanted within a patient's body to support pelvic organs for the treatment of pelvic prolapse.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, a human male, or any other mammal.

FIG. 1 is a schematic diagram of a medical device 100 configured to be implanted within a patient's body. The medical device 100 includes a first elongate member 102 and a second elongate member 104. The first elongate member 102 is coupled to the second elongate member 104 through a coupling member 106.

The first elongate member 102 further includes a head portion and a leg portion. The head portion is configured to be attached to a first bodily portion and the leg portion is configured to be attached to a second bodily portion of the patient. In some embodiments, the first bodily portion is an anterior vaginal wall and the second bodily portion is a sacrum of the patient. Therefore, in accordance with these embodiments, the head portion of the first elongate member 102 is attached to the anterior vaginal wall and the leg portion of the first elongate member 102 is attached to the sacrum or close to the sacrum. In still other embodiments, the second bodily portion can be different from the sacrum.

The second elongate member 104 includes a head portion and a leg portion. The head portion of the second elongate member 104 is configured to be attached to a third bodily portion and the leg portion of the second elongate member 104 is configured to be attached to a fourth bodily portion. In some embodiments, the third bodily portion is a posterior vaginal wall. In some embodiments, the fourth bodily portion can be the sacrum or close to the sacrum. Therefore, in accordance with these embodiments, the head portion of the second elongate member 104 is attached to the anterior vaginal wall and the leg portion of the second elongate member 104 is attached to the sacrum of the patient. In still other embodiments, the fourth bodily portion can be different from the sacrum. In some embodiments, the second bodily portion and the fourth bodily portion are same. In some other embodiments, the second bodily portion and the fourth bodily portion are different.

In some embodiments, the length and shape of the head portion of the first elongate member 102 is different from the length and shape of the head portion of the second elongate member 104. The lengths and shapes of the head portions of the first elongate member 102 and the second elongate member 104 are designed in accordance with the anatomical structure of the first and third bodily portions, respectively, where the head portions are coupled. Similarly, in some embodiments, the length and shape of the leg portion of the first elongate member 102 can be different from the length and shape of the leg portion of the second elongate member 104 because of the difference in the length of the anterior and posterior vaginal walls. For example, the length of the posterior vaginal wall is more than the length of the anterior vaginal wall. So, the leg portion of the second elongate member 104 is required to be greater in length than the leg portion of the first elongate member 102.

In some embodiments, the length of the second elongate member 104 (that is configured to be attached to the posterior vaginal wall and the sacrum) is greater than the length of the first elongate member 102 (that is configured to be attached to the anterior vaginal wall and the sacrum). This difference in the length is mainly provided because of the difference in the anatomical structure of the anterior vaginal wall and the posterior vaginal wall. Similarly, the shape of the head portion of the first elongate member 102 and the second elongate member 104 may vary due to the difference in the anatomical structure. Further, the shape of the leg portion of the first elongate member 102 and the leg portion of the second elongate member 104 may be different. However, in accordance with various other embodiments, the first elongate member 102 and the second elongate member 104 may be identical. In an exemplary embodiment, the head portions and/or the leg portions of the first elongate member 102 and the second elongate member 104 may be identical. The various types of designs, shapes, and lengths of the first elongate member 102 and the second elongate member 104 may be decided by an operator or a surgeon to suit a specific surgery.

In some embodiments, the first elongate member 102 and the second elongate member 104 include mesh strips. The mesh strips are made of a polymeric material that may include a natural and/or a synthetic material. Exemplary polymeric materials are polypropylene, polyester, polyethylene, nylon, PVC, polystyrene, and the like. The mesh strips are preferably made of a non-woven polymeric material. An example of the mesh utilized in the strips is Polyform® Synthetic Mesh developed by the Boston Scientific Corporation. The Polyform® Synthetic Mesh is made from uncoated monofilament macro-porous polypropylene. The mesh may also be made from a biological material or a cadaveric tissue. Typically, the mesh strips have smooth surfaces to avoid/reduce irritation on adjacent body tissues during medical interactions. Additionally, the mesh strips are stretchable and flexible to adapt movements along the anatomy of the human body and reduce suture pullout. Furthermore, softness, lightness, conformity, and strength are certain other attributes required in the mesh strips for efficient tissue repair and implantation.

The coupling member 106 is configured to be coupled to and extend between the first elongate member 102 and the second elongate member 104 to couple the first elongate member 102 with the second elongate member 104 when the medical device 100 is in a first configuration. The first configuration of the medical device 100 is defined when the first elongate member 102 is coupled to the second elongate member 104 through the coupling member 106. In the first configuration, the first elongate member 102 and the second elongate member 104 form a single member.

In some embodiments, the coupling member 106 includes wings or ears that are positioned along the leg portions longitudinally at distinct locations and spaced from one another. The wings are extended portions such as protrusions provided along the longitudinal edges of the elongate members 102 and 104. The wings are provided at places where coupling of the first elongate member 102 and the second elongate members 104 is done. The wings are provided on each of the first elongate member 102 and the second elongate member 104 such that corresponding wings on the first elongate member 102 and the second elongate member 104 can be stitched or attached together, thereby coupling the elongate members 102 and 104. In embodiments, the wings form an integral part of the medical device 100.

In some embodiments, the coupling member 106 may include elements such as sutures, adhesives, bonding agents, mechanical fasteners (e.g. a medical grade plastic clip), and the like to couple the wings provided on the elongate members 102 and 104. These elements (sutures, adhesives, bonding agents, mechanical fasteners, and the like) may be disposed at coupling locations on the coupling member 106. The sutures may be made of biological materials and/or synthetic materials. The sutures may be strong enough to hold both the first elongate member 102 and the second elongate member 104 securely and may also be flexible enough to be knotted.

The coupling member 106 is configured to be decoupled from at least one of the first elongate member 102 and the second elongate member 104 when the medical device 100 is in a second configuration. In the second configuration, the first elongate member 102 and the second elongate member 104 are separated into two different members such that the two decoupled members are configured to be placed at two distinct bodily locations. In some embodiments, decoupling may be done by mere removal or clipping of the wings. Since the wings are extended at the edges of the elongate members 102 and 104, they can be easily clipped. In some other embodiments, decoupling may be done by removal of the sutures, adhesive, staples, and the like, which are used to fasten wings with the elongated members.

FIG. 2A is a top view of a medical device 200 in accordance with an embodiment of the present invention. The medical device 200 includes a first elongate member 202 and a second elongate member 204 in a coupled configuration (first configuration). The first elongate member 202 and the second elongate member 204 are overlaid in the coupled configuration as illustrated in FIG. 2A. The first elongate member 202 includes a head portion 208 and a leg portion 210. The head portion 208 is configured to be attached to a first bodily portion and the leg portion 210 is configured to be attached to a second bodily portion of a patient. In some embodiments, the first bodily portion is an anterior vaginal wall and the second bodily portion is a sacrum of the patient. Therefore, in accordance with these embodiments, the head portion 208 of the first elongate member 202 is attached to the anterior vaginal wall and the leg portion 210 of the first elongate member 202 is attached to the sacrum.

The second elongate member 204 includes a head portion 212 and a leg portion 214. The head portion 212 of the second elongate member 204 is configured to be attached to a third bodily portion and the leg portion 214 of the second elongate member 204 is configured to be attached to a fourth bodily portion. In some embodiments, the third bodily portion is a posterior vaginal wall and the fourth bodily portion is the sacrum. In accordance with the first configuration (coupled configuration) as illustrated in FIG. 2A, the second bodily portion and the fourth bodily portion are the same. Therefore, in accordance with these embodiments, the leg portion 210 of the first elongate member 202 and the leg portion 214 of the second elongate member 204 are attached to the same location—the sacrum. In still other embodiments, the second bodily portion and the fourth bodily portion can be away or different from the sacrum.

In some embodiments, the first elongate member 202 is exclusively designed in accordance with the shape and length of the bodily tissues where it is attached. For example, the head portion 208 of first elongate member 202 may be roughly bulbous with a flat bottom surface. The head portion 208 of the first elongate member 202 is greater in width than the leg portion 210 of the first elongate member 202 to ensure increased surface area contact between the head portion 208 and the anterior vaginal wall. The leg portion 210 of the first elongate member 202 (that is configured to be fixed to anatomical structures located deep within the pelvis such as the sacrum and the like) is roughly a narrow extension extending from the head portion 208.

In some embodiments, the second elongate member 204 is designed in shape and length in accordance with the shape and length of the bodily tissues where it is attached. For example, the head portion 212 of the second elongate member 204 may be roughly bulbous in shape and slightly tapering toward the flat bottom surface. The head portion 212 of the second elongate member 202 is greater in width than the leg portion 214 of the second elongate member 202 to ensure increased surface area contact between the head portion 212 and the posterior vaginal wall. The leg portion 214 of the second elongate member 204 (that is configured to be fixed to anatomical structures located deep within the pelvis such as the sacrum and the like) is roughly a narrow extension extending from the head portion 212.

In some embodiments, the length and shape of the head portion 208 of the first elongate member 202 is different than the length and shape of the head portion 212 of the second elongate member 204. The lengths and shapes of the head portions 208 and 212 of the first elongate member 202 and the second elongate member 204 are designed in accordance with the anatomical structure of the first bodily portion and the third bodily portion, respectively, where the head portions 208 and 212 are coupled. Similarly, in some embodiments, the length and shape of the leg portion 210 of the first elongate member 202 can be different than the length and shape of the leg portion 214 of the second elongate member 204 because of the difference in the length of the anterior vaginal wall and the posterior vaginal wall. For example, the length of the posterior vaginal wall is more than the length of the anterior vaginal wall. So, the leg portion 214 of the second elongate member 204 is required to be greater in length than the leg portion 210 of the first elongate member 202.

As stated above also, various shapes and lengths of the elongate members 202 and 204 and their head portions 208 and 212 and leg portions 210 and 214 are possible according to the requirements. In some embodiments, the length of the second elongate member 204 (that is configured to be attached to the posterior vaginal wall and the sacrum) is greater than the length of the first elongate member 202 (that is configured to be attached to the anterior vaginal wall and the sacrum). This difference in the length is provided mainly because of the difference in the anatomical structure of the anterior vaginal wall and the posterior vaginal wall. Similarly, the shape of the head portion 208 of the first elongate member 202 and the head portion 212 of the second elongate member 204 may vary due to the difference in the anatomical structure. Further, the shape of the leg portion 210 of the first elongate member 202 and the leg portion 214 of the second elongate member 204 may be different. However, in accordance with various other embodiments, the first elongate member 202 and the second elongate member 204 may be identical. In an exemplary embodiment, the head portions 208 and 212 and/or the leg portions 210 and 214 of the first elongate member 202 and the second elongate member 204 may be identical. The various types of designs, shape, and length of the first elongate member 202 and the second elongate member 204 may be decided by an operator or a surgeon to suit a specific surgery.

The material used in the first elongate member 202 and the second elongate member 204 has been described in conjunction with FIG. 1.

As illustrated in FIG. 2A, the first elongate member 202 is coupled to the second elongate member 204 in the first configuration through a coupling member 206. The coupling member 206 is configured to be coupled to and extend between the first elongate member 202 and the second elongate member 204 to couple the first elongate member 202 to the second elongate member 204 when the medical device 200 is in the first configuration.

In some embodiments, the coupling member 206 may be in the form of wings that are positioned along the leg portions 210 and 214 longitudinally at distinct locations and spaced from one another. The wings are extended portions such as protrusions that are provided along the longitudinal edges of the elongate members 202 and 204. The wings are provided at places where coupling of the first elongate member 202 and the second elongate member 204 is done. The wings are provided on each of the first elongate member 202 and the second elongate member 204 such that corresponding wings on the first elongate member 202 and the second elongate member 204 can be stitched or attached together, thereby coupling the elongate members 202 and 204. In embodiments, the wings form an integral part of the elongate members 202 and 204.

The wings may utilize a variety of mesh materials such as polymeric material that may include natural material such as biological material or a cadaveric tissue and the like, and synthetic material such as polypropylene, polyester, polyethylene, nylon, PVC, polystyrene, and the like. The wings may be clipped easily by the surgeon/operator and help them separate the elongate members 202 and 204 with ease. After clipping, the first elongate member 202 and the second elongate member 204 may be attached to the respective bodily portions. The procedure of clipping and placement of the elongate members 202 and 204 inside the patient's body is described later.

In some embodiments, the coupling member 206 may include elements such as sutures, adhesives, bonding agents, mechanical fasteners (e.g. a medical grade plastic clip), and the like to couple the elongate members 202 and 204. The sutures, adhesives, bonding agents, mechanical fasteners, and the like may be disposed at coupling locations on the coupling member 206. The sutures may be made of biological materials and/or synthetic materials. The sutures may be strong enough to hold both the first elongate member 202 and the second elongate member 204 securely and may also be flexible enough to be knotted.

As an exemplary scenario, the coupling member 206 is provided at three distinct locations as illustrated in FIG. 2A. However, in certain other embodiments, the coupling member 206 may be provided at more than three or less than three locations also. Further, the spacing between various coupling members placed at distinct locations may vary based on the design requirements.

Figure 3:
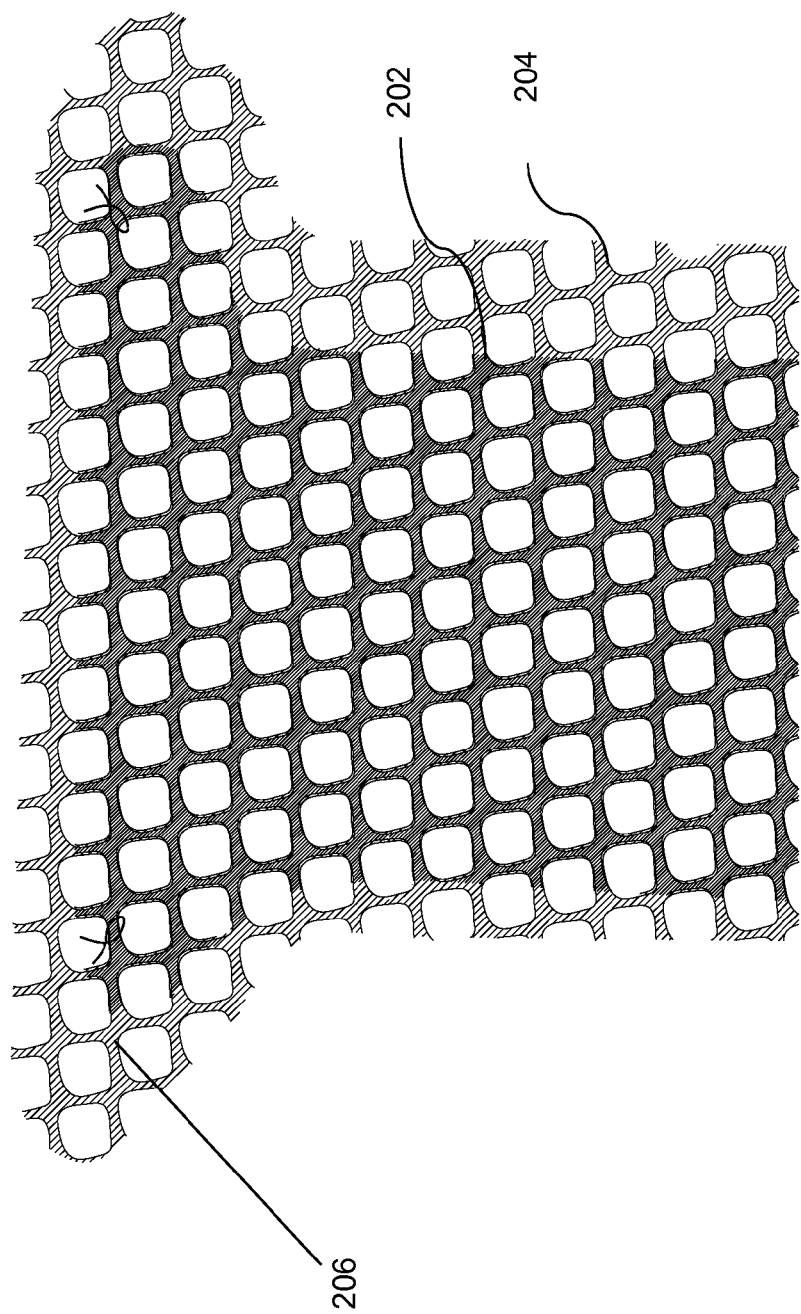
FIG. 3 is an enlarged view of a coupling member, in accordance with an embodiment of the present invention.

An enlarged view of the coupling member 206 including sutures is illustrated in FIG. 3. As illustrated, the coupling member 206 can be in the form of wings that are positioned longitudinally along the leg portions 210 and 214 at distinct locations and spaced from one another. These wings are, in fact, extended portions of the elongate members 202 and 204 at certain distinct locations along the longitudinal edges of the elongate members 202 and 204. The wings are provided at places where coupling of the first elongate member 202 and the second elongate member 204 is done. The wings are provided on each of the first elongate member 202 and the second elongate member 204 such that corresponding wings on the first elongate member 202 and the second elongate member 204 can be stitched or attached together, thereby coupling the elongate members 202 and 204. In embodiments, the wings form an integral part of the medical device 200. As an exemplary scenario illustrated in FIG. 3, the wings of the first elongate member 202 and the second elongate member 204 are stitched using sutures. However, other elements (as discussed above) can also be employed. The wings (extended portions) can be clipped at their distal ends (away from the edges of the elongate members 202 and 204), thereby separating the elongate members 202 and 204.

Referring again to FIG. 2A, the leg portion 210 of the first elongate member 202 overlaps the leg portion 214 of the second elongate member 204 in the first configuration. In some embodiments, the coupled configuration can hold the anterior and posterior vaginal walls with a uniform tension after being secured with bodily tissues. However, in some other embodiments, the tension in the two elongate members 202 and 204 can be different.

In the coupled configuration, the head portions 208 and 212 are configured to be attached to the anterior and the posterior vaginal walls separately, while the leg portions 210 and 214 are configured to be attached to the same location such as the sacrum or close to the sacrum or any other location in the patient's body.

In accordance with some other embodiments, the first elongate member 202 and the second elongate member 204 are configured to be decoupled completely and delivered at distinct locations within the patient's body. FIG. 2B is a perspective illustration of the first elongate member 202 and the second elongate member 204 in a decoupled configuration (second configuration), in accordance with an embodiment of the present invention. As illustrated, the first elongate member 202 and the second elongate member 204 are decoupled from one another completely, and the elongate members 202 and 204 are configured to be delivered and placed independent of one another inside the patient's body. In some embodiments, the second configuration may be achieved by clipping the coupling member 206. Therefore, as shown, the first elongate member 202 and the second elongate member 204 do not possess the coupling member 206 in the second configuration since it has already been clipped. In some other embodiments, the decoupled configuration/state of the elongated members 202 and 204 may be achieved by removing the sutures or the adhesive or any other fastener provided on the coupling member 206. In accordance with these embodiments, the coupling member 206 may still exist on the elongate members 202 and 204 even after clipping. However, the elongate members 202 and 204 are now decoupled.

In accordance with the decoupled configuration, the head portion 208 of the first elongate member 202 is attached to the first bodily portion such as the anterior vaginal wall and the leg portion 210 of the first elongate member 202 is attached to the second bodily portion such as the sacrum or close to the sacrum. The head portion 212 of the second elongate member 204 is attached to the third bodily portion such as the posterior vaginal wall and the leg portion 214 of the second elongate 204 member is attached to the fourth bodily portion such as the sacrum or close to the sacrum. In accordance with the decoupled configuration, the third bodily portion and the fourth bodily can be same or different.

In accordance with the decoupled configuration, the leg portions 210 and 214 are disposed along one another without being overlaid. In certain embodiments, the leg portions 210 and 214 can be disposed in a parallel manner sidewise such as when the leg portions 210 and 214 are attached to the same or similar locations. In some other embodiments, the disposition and arrangement may not be parallel, i.e., when the leg portions 210 and 214 are coupled to different locations. The elongate members 202 and 204, in the decoupled configuration, can hold the bodily tissues with different independent tensions at the anterior and posterior vaginal walls. It is easier for an operator to adjust tensions of the first elongate member 202 and the second elongate member 204 independently in the decoupled configuration. However, in some embodiments, the tensions in the first elongate member 202 and the second elongate member 204 can the same.

In accordance with some embodiments, the medical device 200 or a portion of the medical device 200 is made of blue color that assists in visualization of the medical device 200 during placement and/or repair. In some other embodiments, any color other than blue may be employed for easy visualization.

Figure 4A:
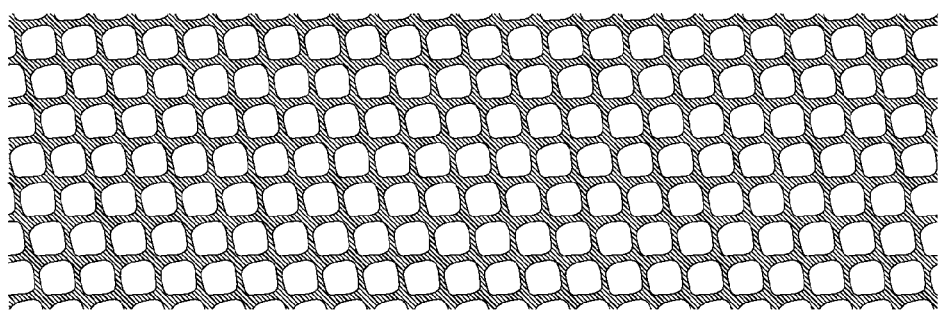
FIG. 4A is a perspective illustration of a weave pattern of a medical device, in accordance with an embodiment of the present invention.

FIG. 4A is a perspective illustration of a weave pattern of the medical device 200, in accordance with an embodiment of the present invention. The weave pattern is hereafter described with respect to the medical device 200. However, in accordance with other embodiments, the weave pattern may be employed in the medical device 100 also.

The elongate members 202 and 204 include a bias cut weave pattern such that threads of the weave pattern are machined along a longitudinal direction substantially parallel to the lengths of the elongate members 202 and 204. The bias cut weave pattern provides square shaped cells as shown in FIG. 4A. The square shaped cells obtained as a result of the bias cut provide less stretchability to the elongate members 202 and 204 along their lengths. In this manner, any stretching of the elongate members 202 and 204 during bodily interactions does not affect tensions provided to the elongate members 202 and 204 upon placement (which is a requirement for the treatment of a problem such as prolapse). The elongate members 202 and 204 are, therefore, still held with the same tensions even after stretching.

Figure 4B:
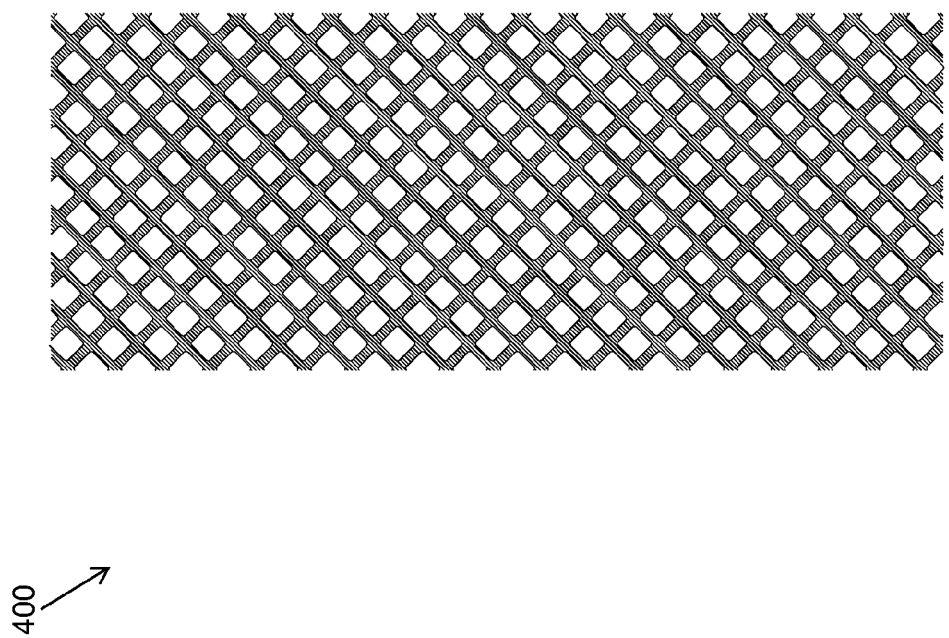
FIG. 4B is a perspective illustration of a weave pattern of a medical device, in accordance with an embodiment of another invention.

In accordance with some other embodiments, conventional designs of the mesh such as a mesh having diamond shaped cells may also be employed in the elongate members 202 and 204. The mesh having the diamond shaped cells is illustrated in FIG. 4B. The diamond shaped cells provide more stretchability to the elongate members 202 and 204 along their lengths as compared to the square shaped cells discussed above in FIG. 4A.

Figure 5A:
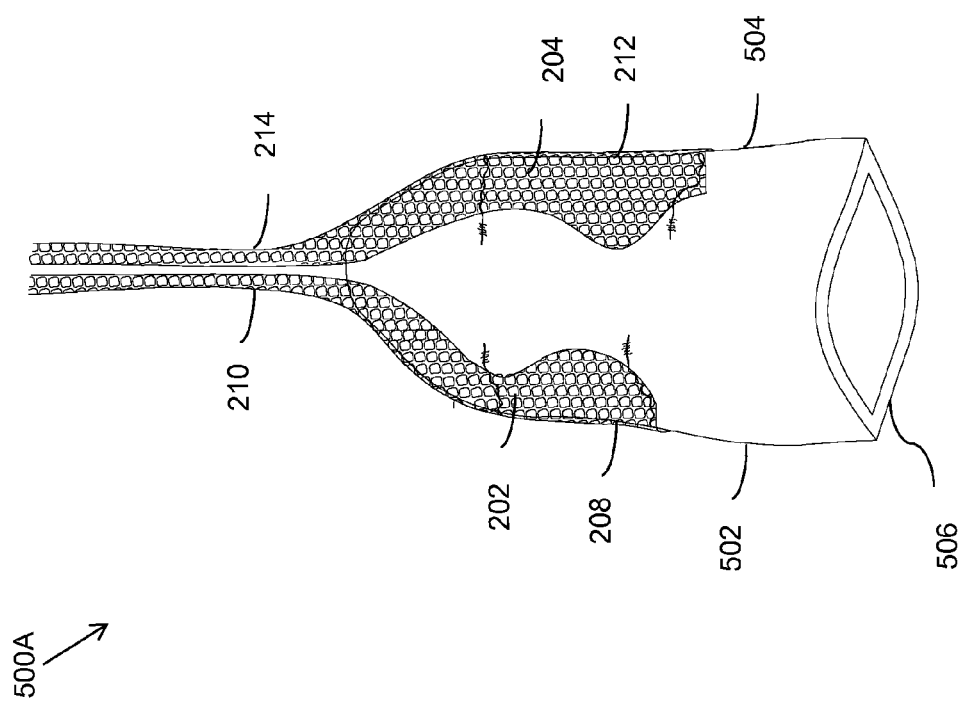
FIGS. 5A-5C illustrate schematic views of placement of a medical device in the second configuration (decoupled configuration), in accordance with an embodiment of the present invention.
Figure 5B:
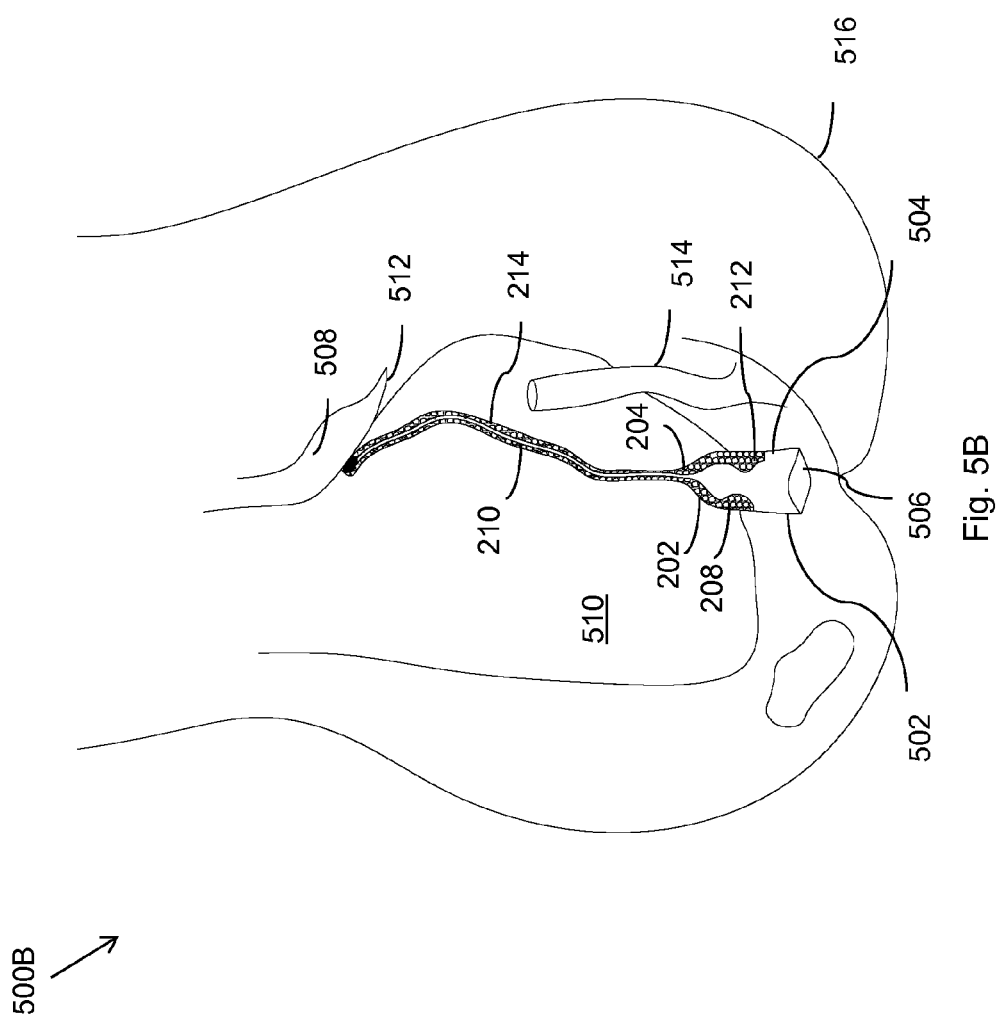
Figure 5C:
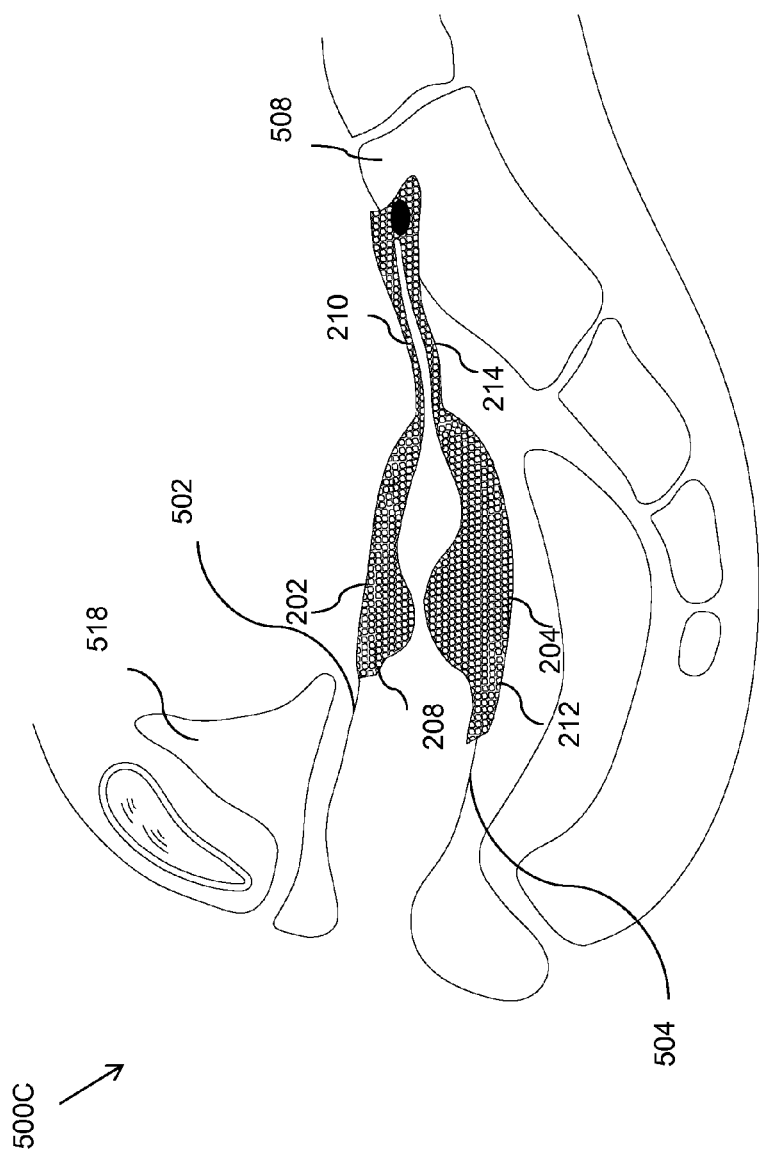

FIGS. 5A-5C illustrate various perspective views of the placement of the medical device 200 in the second configuration (decoupled configuration), in accordance with an embodiment of the present invention. The body portions of the patient such as an anterior vaginal wall 502, a posterior vaginal wall, 504, a vagina 506, a sacrum 508, a peritoneal cavity 510, a coccyx 512, a rectum 514, buttocks 516 and a bladder 518 are illustrated in FIGS. 5A-5C.

The head portion 208 of the first elongate member 202 is attached to the anterior vaginal wall 502 of the vagina 506 and the leg portion 210 of the first elongate member 202 is attached to the sacrum 508. The head portion 212 of the second elongate member 204 is attached to the posterior wall 504 of the vagina 506 and the leg portion 214 of the second elongate member 204 is attached to the sacrum 508. In some embodiments, the head portions 208 and 212 and the leg portions 210 and 214 of the first elongate member 202 and the second elongate member 204 are designed in shape and length in accordance with the anatomical structure of the coupling locations/bodily tissues at the anterior vaginal wall 502, posterior vaginal wall 504, and the sacrum 508.

In accordance with the decoupled configuration, the leg portions 210 and 214 are disposed along one another without being overlaid. In certain embodiments, the leg portions 210 and 214 can be disposed in a parallel manner i.e., when the leg portions 210 and 214 are attached to the same or similar locations. In some other embodiments, the disposition and arrangement may not be parallel when the leg portions 210 and 214 are coupled to different locations. The decoupled configuration holds the bodily tissues with different independent tensions at the anterior and posterior vaginal walls 502 and 504. However, in some embodiments, the tensions at the anterior and posterior vaginal walls 502 and 504 can be the same.

Figure 5F:
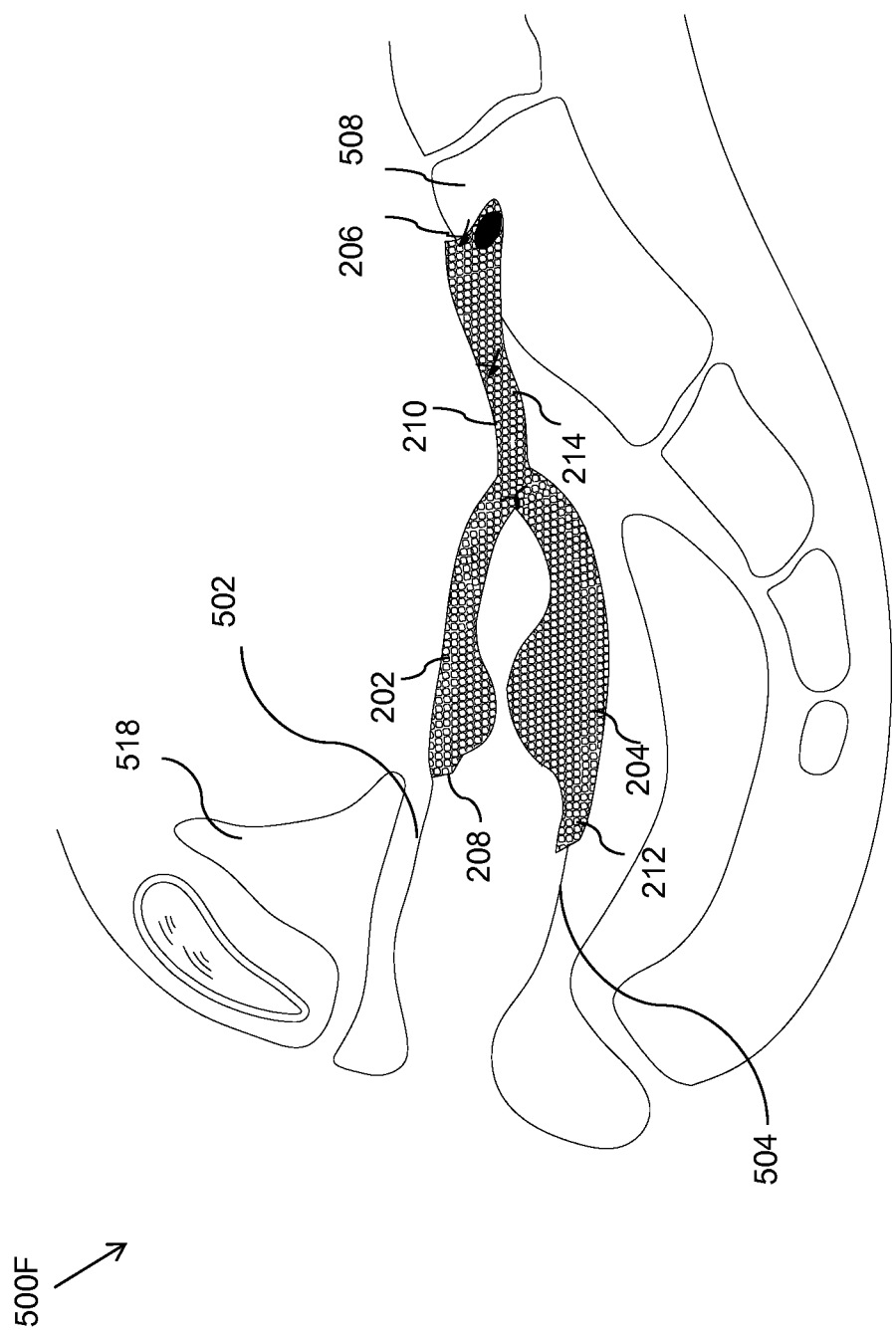

FIGS. 5D-5F illustrate various perspective views of the placement of the medical device 200 in the first configuration (coupled configuration), in accordance with an embodiment of the present invention. As shown, the head portion 208 of the first elongate member 202 is attached to the anterior wall 502 of the vagina 506 and the leg portion 210 of the first elongate member 202 is attached to the sacrum 508. The head portion 212 of the second elongate member 204 is attached to the posterior wall 504 of the vagina 506 and the leg portion 214 of the second elongate member 204 is attached to the sacrum 508. The leg portion 210 of the first elongate member 202 overlaps the leg portion 214 of the second elongate member 204 in the first configuration upon placement. In some embodiments, the coupled configuration holds the anterior and posterior vaginal walls 502 and 504 with a uniform tension after being secured with the bodily tissues. In some other embodiments, the anterior and posterior vaginal walls 502 and 504 can be held with different tensions.

FIG. 6 is a flowchart illustrating a method 600 of placement of a medical device such as the medical device 100 or the medical device 200, in accordance with an embodiment of the present invention.

Referring now to FIG. 6 in conjunction with FIGS. 5A-5C, the method of placement of the medical device 200 is described in accordance with an embodiment of the present invention. The medical device 200 is hereafter used to describe the placement in an exemplary embodiment. However, it must be appreciated that the medical device 100 may also be placed in the similar manner.

The method 600 includes creating an abdominal access to the vagina 506 of a patient for delivery of the medical device 200 at step 602. The medical device 200 includes the first elongate member 202, the second elongate member 204, and the coupling member 206. The first elongate member 202 further includes the head portion 208 and the leg portion 210, and the second elongate member 204 further includes the head portion 212 and the leg portion 214. The coupling member 206 is configured to be coupled to and extend between the first elongate member 202 and the second elongate member 204. The medical device 200 has been described in conjunction with FIG. 2. In accordance with various embodiments, an operator or a surgeon may make abdominal incisions laproscopically, laprotomically, or in any other manner.

The method further includes decoupling the coupling member 206 at step 604 from at least one of the first elongate member 202 and the second elongate member 204 such that the first elongate member 202 and the second elongate member 204 are separated from one another. The first elongate member 202 and the second elongate member 204 are decoupled into two different members such that the two decoupled members are configured to be placed at two distinct bodily locations. In some embodiments, decoupling may be done by mere removal or clipping of the coupling member 206 (such as wings). In some other embodiments, decoupling may be done by removal of the sutures, adhesive, staples and the like, which are used to fasten wings with the elongated members 202 and 204. The coupling member 206, sutures, and other fastening members are discussed in detail in conjunction with FIGS. 1 and 2. The decoupled state/configuration of the medical device 200 is referred to as the second configuration.

Once the first elongate member 202 is decoupled from the second elongate member 204, the first elongate member 202 and the second elongate member 204 are inserted into a body opening at step 606. The first elongate member 202 and the second elongate member 204 may be inserted into the peritoneal cavity 510 through the laparoscopic or the laparotomic surgery via holes in the abdomen wall.

The head portion 208 of the first elongate member 202 is then attached to the anterior vaginal wall 502 at step 608. In some embodiments, the first elongate member 202 is designed in shape and length in accordance with the anatomical structure of the coupling locations (where the elongate member is coupled/attached to the bodily tissues) at the anterior vaginal wall 502.

The head portion 512 of the second elongate member 204 is then attached to the posterior vaginal wall 504 at step 610. In some embodiments, the second elongate member 204 is designed in shape and length in accordance with the anatomical structure of the coupling locations (where the elongate member is coupled/attached to the bodily tissues) at the posterior wall 504.

Subsequently, the leg portion 210 of the first elongate member 202 and the leg portion 214 of the second elongate member 204 are attached to the sacrum 508 of the patient at step 612. In some other embodiments, the leg portions 210 and 214 can be attached to different locations close to the sacrum 508 or any other body locations. The leg portion 210 of the first elongate member 202 fits along the leg portion 214 of the second elongate member 204 without being overlaid. In some embodiments, the first elongate member 202 and the second elongate member 204 can hold the respective bodily tissues with different and independent tensions at the anterior and posterior vaginal walls 502 and 504. However, in some other embodiments, the respective bodily tissues can be held with the same tensions also. The abdominal incisions may be finally sutured after attachment of the elongate members 502 and 504. In some embodiments, the operator/surgeon can adjust tension of the first elongate member 202 and the second elongate member 204.

The procedure of placement of the medical device 200 in the second configuration has been described above. It must be appreciated that the beauty of the present invention is the use of the medical device 200 in either of the two configurations—the first configuration and the second configuration. Therefore, the medical device 200 may be delivered and placed inside the patient's body in the first configuration also, as illustrated in FIGS. 5D-5F. In accordance with this scenario, the first elongate member 202 and the second elongate member 204 are coupled together. Therefore, the leg portion 210 of the first elongate member 202 and the leg portion 214 of the second elongate member 204 overlap one another after placement, and accordingly a uniform tension can be provided to both the elongate members 202 and 204. Though, in some other embodiments, different tensions can be provided in this configuration also. Therefore, the surgeon or the operator may decide the configuration that best fits for a particular case of surgery and accordingly configure the medical device 200 in either of the configurations.

In some embodiments, a medical device is configured to be delivered and placed within a patient's body. The medical device includes a first elongate member, a second elongate member, and a coupling member. The first elongate member has a leg portion and a head portion. The head portion is configured to be attached to a first bodily portion and the leg portion is configured to be attached to a second bodily portion. The second elongate member has a leg portion and a head portion. The head portion is configured to be attached to a third bodily portion and the leg portion is configured to be attached to a fourth bodily portion. The is configured to be coupled to and extend between the first elongate member and the second elongate member to couple the first elongate member to the second elongate member when the medical device is in a first configuration. The coupling member is configured to be decoupled from at least one of the first elongate member and the second elongate member when the medical device is in a second configuration.

In some embodiments, the medical device is configured to support pelvic organs for the treatment of pelvic prolapse. In some embodiments, the first elongate member and the second elongate member comprise a polypropylene mesh. In some embodiments, the first elongate member and the second elongate member comprise a non-woven polymeric material. In some embodiments, the first bodily portion is an anterior vaginal wall such that the head of the first elongate member is attached to the anterior vaginal wall. In some embodiments, the second bodily portion and the fourth bodily portion includes a sacrum such that the leg portion of the first elongate member and the leg portion of the second elongate member are attached to a same location. In some embodiments, the second bodily portion and the fourth bodily portion are different such that the leg portion of the first elongate member and the leg portion of the second elongate member are attached to different locations. In some embodiments, the third bodily portion is a posterior vaginal wall such that the head portion of the second elongate member is attached to the posterior vaginal wall. In some embodiments, the first elongate member comprises a shape in conformation to an anatomy of an anterior vaginal wall. In some embodiments, the second elongate member comprises a shape in conformation to an anatomy of a posterior vaginal wall. In some embodiments, the leg portion of the first elongate member comprises a narrower section than the head portion of the first elongate member. In some embodiments, the leg portion of the second elongate member comprises a narrower section than the head portion of the second elongate member. In some embodiments, the coupling member comprises wings placed along the leg portion of the first elongate member and the leg portion of the second elongate member such that the wings are configured to be clipped. In some embodiments, the first elongate member overlaps the second elongate member in the first configuration upon placement.

In some embodiments, the leg portion of the first elongate member fits along the leg portion of the second elongate member in a parallel manner in the second configuration upon placement. In some embodiments, the medical device is blue in color configured to assist in visualization of the medical device during placement and repair. In some embodiments, the first elongate member and the second elongate member include a weave pattern such that threads of the weave pattern are machined along a longitudinal direction substantially parallel to lengths of the first elongate member and the second elongate member. In some embodiments, the weave pattern of the first elongate member and the second elongate is bias cut. In some embodiments, the weave pattern provides square shaped cells to the first elongate member and the second elongate member.

In some embodiments, a method of implanting a medical device in a patient's body includes creating an abdominal access to a vagina of the patient for delivery of the medical device, the medical device having a first elongate member including a leg portion and a head portion and a second elongate member including a leg portion and a head portion and a coupling member, the coupling member being configured to be coupled to and extend between the first elongate member and the second elongate member; decoupling the coupling member from at least one of the first elongate member and the second elongate member such that the first elongate member and the second elongate member are separated; inserting the first elongate member and the second elongate member into a body opening; attaching the head portion of the first elongate member to an anterior vaginal wall; attaching the head portion of the second elongate member to a posterior vaginal wall; and attaching the leg portion of the first elongate member and the leg portion of the second elongate member to a sacrum of the patient.

In some embodiments, the abdominal access is created laproscopically. In some embodiments, the abdominal access is created laprotomically.

In some embodiments, the method includes clipping the coupling member to transform the first configuration into the second configuration. In some embodiments, the method includes adjusting tensions of the first elongate member and the second elongate member.

In some embodiments, the attaching the leg portion of the first elongate member and the leg portion of the second elongate member to the sacrum comprises attaching the leg portion of the first elongate member and the leg portion of the second elongate member in an overlap manner. In some embodiments, the attaching the leg portion of the first elongate member and the leg portion of the second elongate member to the sacrum comprises attaching the leg portion of the first elongate member and the leg portion of the second elongate member in a sidewise manner.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device configured to be delivered and placed within a patient's body, the medical device comprising:
   a first elongate member having a mesh leg portion and a head portion, the head portion of the first elongate member configured to be attached to a first bodily portion and the mesh leg portion of the first elongate member configured to be attached to a second bodily portion, the first bodily portion being an anterior vaginal wall;
   a second elongate member having a mesh leg portion and a head portion, the head portion of the second elongate member configured to be attached to a third bodily portion and the mesh leg portion of the second elongate member configured to be attached to a fourth bodily portion; and
   a coupling member, the coupling member being configured to be coupled to and extend between the first elongate member and the second elongate member to couple the first elongate member to the second elongate member when the medical device is in a first configuration, the coupling member being configured to be decoupled from at least one of the first elongate member and the second elongate member when the medical device is in a second configuration, the mesh leg portion of the first elongate member at least partially overlying and coupled, via the coupling member with the mesh leg portion of the second elongate member when the medical device is in the first configuration, the mesh leg portion of the first elongate member being decoupled from the mesh leg portion of the second elongate member in the second configuration.

2. The medical device of claim 1, wherein the first elongate member and the second elongate member include a weave pattern such that threads of the weave pattern are machined along a longitudinal direction substantially parallel to lengths of the first elongate member and the second elongate member.

3. The medical device of claim 2, wherein the weave pattern of the first elongate member and the second elongate is bias cut.

4. The medical device of claim 2, wherein the weave pattern provides square shaped cells to the first elongate member and the second elongate member.

5. The medical device of claim 1, wherein the medical device is configured to support pelvic organs for treatment of pelvic prolapse.

6. The medical device of claim 1, wherein the first elongate member and the second elongate member are formed from a polypropylene mesh.

7. The medical device of claim 1, wherein the head portion of the first elongate member and the head portion of the second elongate member include a non-woven polymeric material.

8. The medical device of claim 1, wherein the second bodily portion and the fourth bodily portion includes a sacrum such that the leg portion of the first elongate member and the leg portion of the second elongate member are attached to a same location.

9. The medical device of claim 1, wherein the second bodily portion and the fourth bodily portion are different such that the leg portion of the first elongate member and the leg portion of the second elongate member are attached to different locations.

10. The medical device of claim 1, wherein the third bodily portion is a posterior vaginal wall.

11. The medical device of claim 1, wherein the first elongate member comprises a shape in conformation to an anatomy of an anterior vaginal wall.

12. The medical device of claim 1, wherein the second elongate member comprises a shape in conformation to an anatomy of a posterior vaginal wall.

13. The medical device of claim 1, wherein the leg portion of the first elongate member comprises a narrower section than the head portion of the first elongate member.

14. The medical device of claim 1, wherein the leg portion of the second elongate member comprises a narrower section than the head portion of the second elongate member.

15. The medical device of claim 1, wherein the coupling member comprises wings placed along the leg portion of the first elongate member and the leg portion of the second elongate member such that the wings are configured to be clipped.

16. The medical device of claim 1, wherein the first elongate member overlaps the second elongate member in the first configuration upon placement.

17. The medical device of claim 1, wherein the leg portion of the first elongate member fits along the leg portion of the second elongate member in a parallel manner in the second configuration upon placement.

18. The medical device of claim 1, wherein the medical device is blue in color configured to assist in visualization of the medical device during placement and repair.

19. A method of implanting a medical device in a patient's body, the method comprising:

creating an abdominal access to a body of the patient for delivery of the medical device, the medical device having a first elongate member including a leg portion and a head portion and a second elongate member including a leg portion and a head portion and a coupling member, the coupling member being configured to be coupled to and extend between the first elongate member and the second elongate member;

decoupling the coupling member from at least one of the first elongate member and the second elongate member such that the first elongate member and the second elongate member are separated;

inserting the first elongate member and the second elongate member into a body opening;

attaching the head portion of the first elongate member to a first portion of a bodily organ of the patient on a first side of the bodily organ;

attaching the head portion of the second elongate member to a second portion of the bodily organ on a second side of the bodily organ the second side being opposite the first side;

attaching the leg portion of the first elongate member to a third portion of the bodily organ on the first side of the bodily organ;

and attaching the leg portion of the second elongate member to a fourth portion of the bodily organ on the second side of the bodily such that the leg portion of the first elongate member is substantially parallel with, at least partially overlies and is coupled with the leg portion of the second elongate member.

* * * * *